US00PP31031P2

(12) United States Plant Patent
Kobayashi

(10) Patent No.: US PP31,031 P2
(45) Date of Patent: Nov. 5, 2019

(54) COLEUS PLANT NAMED 'DOCOGREFALIG'

(50) Latin Name: *Solenostemon scutellarioides*
Varietal Denomination: Docogrefalig

(71) Applicant: DUMMEN GROUP B.V., De Lier (NL)

(72) Inventor: Ruth Kobayashi, Carlsbad, CA (US)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/932,824

(22) Filed: Apr. 30, 2018

(51) Int. Cl.
*A01H 5/12* (2018.01)
*A01H 6/50* (2018.01)

(52) U.S. Cl.
USPC ..... Plt./469

(58) Field of Classification Search
USPC ..... Plt./263.1, 469
See application file for complete search history.

(56) References Cited

PUBLICATIONS

Dummen Orange Great Falls Trailing Coleus 2017-2018 season. https://www.billmooreco.com/Dummen%20Orange_Great%20Falls%20Coleus.pdf. 11 pages.*

* cited by examiner

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Coleus* plant named 'Docogrefalig', characterized by its compact to outwardly spreading to trailing plant habit; moderately vigorous growth habit; freely branching habit; variegated leaves that are greyed purple and light green yellow with light green-colored margins; and good garden performance.

1 Drawing Sheet

Botanical designation: *Solenostemon scutellarioides.*
Cultivar denomination: 'DOCOGREFALIG'.

CROSS-REFERENCED TO CLOSELY-RELATED APPLICATIONS

Title: *Coleus* Plant Named 'Docogrefayo'
Applicant: Ruth Kobayashi
Filed: Concurrently with this application; U.S. Plant patent application Ser. No. 15/932,826.
Title: *Coleus* Plant Named 'Docogrefang'
Applicant: Ruth Kobayashi
Filed: Concurrently with this application; U.S. Plant patent application Ser. No. 15/932,825.

BACKGROUND OF THE INVENTION

The present invention relates to a new and distinct cultivar of *Coleus* plant, botanically known as *Solenostemon scutellarioides* and hereinafter referred to by the name 'Docogrefalig'.

The new *Coleus* plant is a naturally-occurring whole plant mutation of a proprietary selection of *Solenostemon scutellarioides* identified as code designation CS-0099, not patented. The new *Coleus* plant was discovered and selected by the Inventor as a single plant within a population of plants of the selection parent in a controlled greenhouse environment in Encinitas, Calif. on Jun. 17, 2016.

Asexual reproduction of the new *Coleus* plant by terminal cuttings in a controlled greenhouse environment in Encinitas, Calif. since August, 2016 has shown that the unique features of this new *Coleus* plant are stable and reproduced true to type in successive generations.

SUMMARY OF THE INVENTION

The new *Coleus* plant has not been observed under all possible combinations of cultural practices and environmental conditions. The phenotype may vary somewhat with variations in environment and cultural practices such as temperature and light intensity without, however, any variance in genotype.

The following traits have been repeatedly observed and are determined to be the unique characteristics of 'Docogrefalig'. These characteristics in combination distinguish 'Docogrefalig' as a new and distinct *Coleus* plant:

1. Compact to outwardly spreading to trailing plant habit.
2. Moderately vigorous growth habit.
3. Freely branching habit.
4. Variegated leaves that are greyed purple and light green yellow with light green-colored margins.
5. Good garden performance.

Plants of the new *Coleus* differ primarily from plants of the mutation parent selection in leaf color as plants of the mutation parent have red purple-colored leaves with bright green-colored margins.

Plants of the new *Coleus* differ primarily from plants of *Solenostemon scutellarioides* 'Docogrefayo', disclosed in a U.S. Plant Patent application filed concurrently, in leaf color as plants of 'Docogrefayo' have light green and light yellow green variegated leaves.

Plants of the new *Coleus* differ primarily from plants of *Solenostemon scutellarioides* 'Docogrefang', disclosed in a U.S. Plant Patent application filed concurrently, in leaf color as plants of 'Docogrefang' have variegated leaves that are greyed purple, greyed orange and light yellow with light green-colored margins.

Plants of the new *Coleus* can be compared to plants of *Solenostemon scutellarioides* 'Witch Doctor', disclosed in U.S. Plant Pat. No. 20,887. In side-by-side comparisons plants of the new *Coleus* differ from plants of 'Witch Doctor' in the following characteristics:

1. Plants of the new *Coleus* are more compact than and not as upright as plants of 'Witch Doctor'.
2. Plants of the new *Coleus* have smaller leaves than plants of 'Witch Doctor'.
3. Leaves of plants of the new *Coleus* have crenate margins whereas leaves of plants of 'Witch Doctor' have deeply lobed leaves.
4. Plants of the new *Coleus* and 'Witch Doctor' differ in leaf color as plants of 'Witch Doctor' have green-colored leaves with dark purple-colored margins and venation.

Plants of the new *Coleus* can also be compared to plants of *Solenostemon scutellarioides* 'Plum Good', disclosed in U.S. Plant Pat. No. 14,425. In side-by-side comparisons plants of the new *Coleus* differ from plants of 'Plum Good' in the following characteristics:

1. Plants of the new *Coleus* are more trailing than and not as outwardly spreading as plants of 'Plum Good'.
2. Plants of the new *Coleus* and 'Plum Good' differ in leaf color as plants of 'Plum Good' have dark burgundy and bright purple bi-colored leaves with gold-colored leaf margins.

BRIEF DESCRIPTION OF THE PHOTOGRAPHS

The accompanying colored photographs illustrate the overall appearance of the new *Coleus* showing the colors as true as it is reasonably possible to obtain in colored reproductions of this type. Colors in the photographs may differ slightly from the color values cited in the detailed botanical description which accurately describe the colors of the new *Coleus*.

The photograph at the bottom of the sheet comprises a side perspective view of a typical plant of 'Docogrefalig' grown in a container.

The photograph at the top of the sheet is a close-up view of a typical plant of 'Docogrefalig'.

DETAILED BOTANICAL DESCRIPTION

The aforementioned photographs and following observations, measurements and values describe plants grown in Encinitas, Calif. in 10-cm containers in a polyethylene-covered greenhouse during the winter and under cultural practices which closely approximate commercial *Coleus* production. During the production of the plants, day temperatures averaged 26° C., night temperatures averaged 18° C. and light levels ranged from 4,500 to 5,500 foot-candles. Plants were ten weeks old when the photographs and the description were taken. In the following detailed description, color references are made to The Royal Horticultural Society Colour Chart, 2007 Edition, except where general terms of ordinary dictionary significance are used.

Botanical classification: *Solenostemon scutellarioides* 'Docogrefalig'.

Parentage: Naturally-occurring whole plant mutation of a proprietary selection of *Solenostemon scutellarioides* identified as code designation CS-0099, not patented.

Propagation:

*Type*.—By terminal cuttings.

*Time to initiate roots, summer and winter*.—About four to six days at night temperatures about 20° C.

*Time to produce a rooted young plant, summer and winter*.—About three weeks at night temperatures about 20° C.

*Root description*.—Fine, fibrous; typically white in color, actual color of the roots is dependent on substrate composition, water quality, fertilizers, substrate temperature and age of roots.

*Rooting habit*.—Freely branching; dense.

Plant description:

*Plant and growth habit*.—Compact, upright to outwardly spreading plant habit; moderately vigorous growth habit and moderate growth rate; freely branching habit with about six to seven primary lateral branches each with about four secondary lateral branches developing per plant.

*Plant height*.—About 11.5 cm.

*Plant diameter*.—About 23.5 cm.

Lateral branch description:

*Length*.—About 11 cm.

*Diameter*.—About 4 mm.

*Internode length*.—About 3.6 cm.

*Strength*.—Strong.

*Aspect*.—About 45° from vertical.

*Texture and luster*.—Minute pubescence; matte.

*Color, when developing and fully developed*.—Close to 146C.

Leaf description:

*Arrangement*.—Opposite, simple.

*Length*.—About 3 cm.

*Width*.—About 3.7 cm.

*Shape*.—Roughly deltoid.

*Apex*.—Acute.

*Base*.—Truncate.

*Margin*.—Broadly crenate.

*Texture and luster, upper and lower surfaces*.—Pubescent, not rugose; matte.

*Venation pattern*.—Pinnate, reticulate.

*Color*.—Developing leaves, upper surface: Center, close to 187B; towards the margins, close to 144A. Developing leaves, lower surface: Close to 146C. Fully expanded leaves, upper surface: Center, close to 187B; towards the base, close to 1B; margins, close to 144A; venation, close to 187B. Fully expanded leaves, lower surface: Close to 148A to 148B; venation, close to 148B.

*Petioles*.—Length: About 2.2 cm. Diameter: About 2 mm. Strength: Strong. Texture and luster: Minute pubescence; matte. Color, upper and lower surfaces: Close to 146C.

Flower description: To date, flower development has not been observed on plants of the new *Coleus*.

Pathogen & pest resistance: To date, plants of the new *Coleus* have not been observed to be resistant to pests and pathogens common to *Coleus* plants.

Garden performance: Plants of the new *Coleus* have been observed to tolerate wind, rain, full sunlight and have good garden performance.

It is claimed:

1. A new and distinct *Coleus* plant named 'Docogrefalig' as illustrated and described.

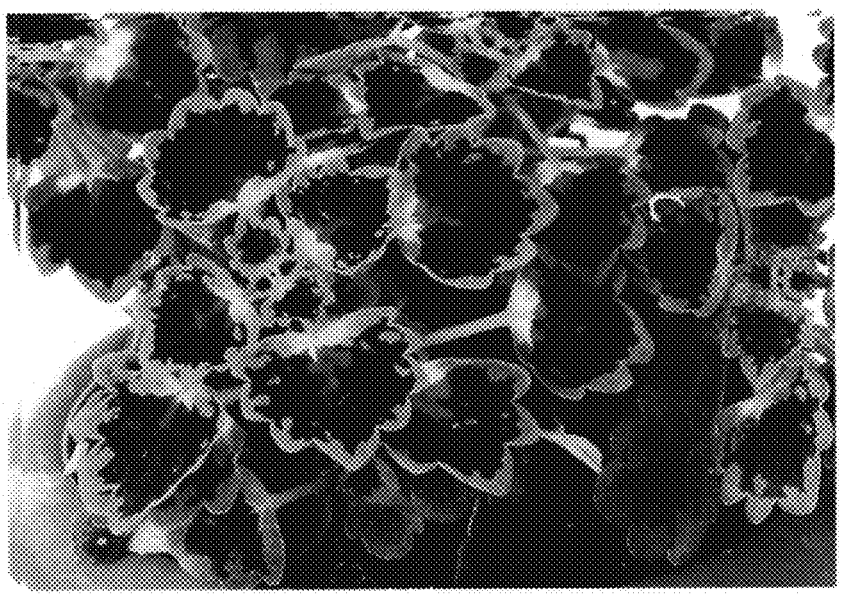
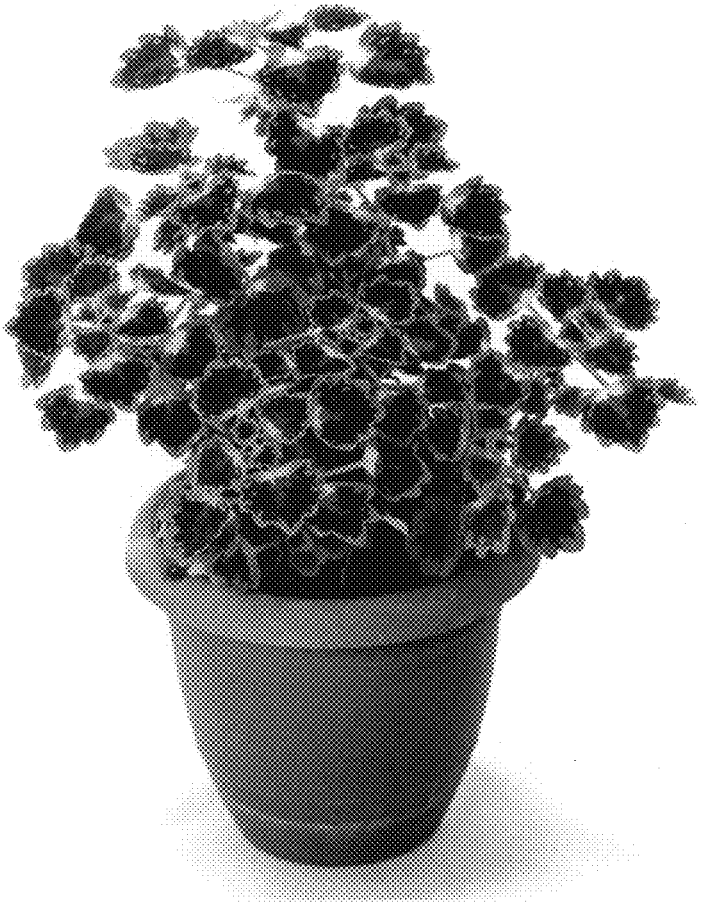

* * * * *